(12) United States Patent
Mondet et al.

(10) Patent No.: US 6,770,271 B2
(45) Date of Patent: *Aug. 3, 2004

(54) POLYESTER POLYURETHANES, PROCESS FOR PREPARING THEM, PSEUDOLATICES PRODUCED FROM THE SAID POLYESTER POLYURETHANES AND THEIR USE IN COSMETIC COMPOSITIONS

(75) Inventors: Jean Mondet, Drancy (FR); Bertrand Lion, Livry-Gargan (FR); Nathalie Mougin, Paris (FR); Bertrand Piot, La Garenne-Colombes (FR); Valérie de La Poterie, Le Chatelet En Brie (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/511,073

(22) Filed: Feb. 23, 2000

(65) Prior Publication Data

US 2003/0191271 A1 Oct. 9, 2003

Related U.S. Application Data

(62) Division of application No. 09/146,521, filed on Sep. 3, 1998, now Pat. No. 6,106,813, which is a continuation-in-part of application No. 08/652,943, filed on May 24, 1996, now abandoned, which is a division of application No. 08/283,765, filed on Aug. 1, 1994, now abandoned.

(30) Foreign Application Priority Data

Aug. 4, 1993 (FR) .............................. 93 09608

(51) Int. Cl.$^7$ .............................. A61K 7/00; A61K 7/02; C08J 3/03; C08L 75/06
(52) U.S. Cl. .................................. 424/70.11; 424/70.17; 424/401; 524/591; 524/839; 524/840; 528/71; 528/80; 528/83
(58) Field of Search .......................... 424/70.11, 70.17, 424/401; 524/839, 840, 591; 528/71, 80, 83

(56) References Cited

U.S. PATENT DOCUMENTS

| | | | |
|---|---|---|---|
| 3,518,045 A | 6/1970 | Rellensmann et al. | 528/74 |
| 3,658,939 A | 4/1972 | Carpenter et al. | 528/83 |
| 3,975,350 A | 8/1976 | Hudgin et al. | 524/108 |
| 3,993,614 A | 11/1976 | Carlson | 427/393 |
| 4,426,487 A | 1/1984 | Konig et al. | 524/710 |
| 4,496,675 A | 1/1985 | Hille et al. | 524/77 |
| 4,554,308 A | 11/1985 | Rusiello | 524/591 |
| 4,743,673 A | 5/1988 | Johnston et al. | 528/60 |
| 5,011,881 A | 4/1991 | Fujii et al. | 524/457 |
| 5,120,529 A | 6/1992 | Koch et al. | 424/61 |
| 5,199,980 A | 4/1993 | Lynch et al. | 106/311 |
| 5,538,717 A | 7/1996 | La Poterie | 424/61 |
| 5,626,840 A | 5/1997 | Thomaides et al. | 424/70.11 |
| 5,643,581 A | 7/1997 | Mougin et al. | 424/401 |
| 6,106,813 A * | 8/2000 | Mondet et al. | 424/61 |

FOREIGN PATENT DOCUMENTS

| | | |
|---|---|---|
| EP | 0076956 | 4/1983 |
| EP | 0391322 | 10/1990 |
| EP | 0418469 | 3/1991 |
| FR | 1457975 | 12/1965 |
| FR | 2708615 | 2/1995 |

* cited by examiner

Primary Examiner—Rabon Sergent
(74) Attorney, Agent, or Firm—Oliff & Berridge, PLC

(57) ABSTRACT

The present invention relates to polyurethanes and a process for preparing them. These polyester polyurethanes contain units corresponding to the following formulae (I) and (II):

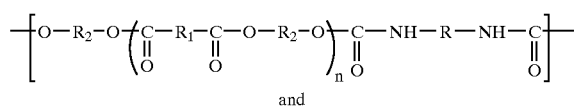

and

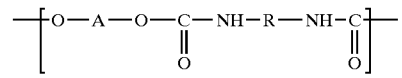

The polyester polyurethanes according to the present invention form pseudolatices and may be utilized as film-forming resin in cosmetic compositions.

60 Claims, No Drawings

POLYESTER POLYURETHANES, PROCESS FOR PREPARING THEM, PSEUDOLATICES PRODUCED FROM THE SAID POLYESTER POLYURETHANES AND THEIR USE IN COSMETIC COMPOSITIONS

This is a Division of application Ser. No. 09/146,521 filed Sep. 3, 1998, now U.S. Pat. No. 6,106,813, which in turn is a continuation-in-part of application Ser. No. 08/652,943 filed May 24, 1996, now abandoned, which in turn is a divisional of application Ser. No. 08/283,765, flied Aug. 1, 1994, now abandoned. The entire disclosure of the prior applications is hereby incorporated by reference herein in its entirety.

FIELD OF THE INVENTION

The present invention relates to a new family of polyester polyurethanes film-forming resins, to a process for preparing them, to pseudolatices produced using said polyester polyurethanes resins and also to cosmetic compositions containing said pseudolatices.

BACKGROUND

It is common practice to use polyurethanes as film-forming resin in many cosmetic formulations, and in particular in different make-up products such as nail varnishes, mascaras and eyeliners. To be satisfactory, the resin must possess not only good film-forming properties, but also good staying properties, that is to say must be difficult to remove from its support by simply washing with water or by means of detergents.

In Patent Application EP 418,469, nail varnish compositions containing aqueous dispersions of aliphatic polyurethanes as film-forming resin have been described.

In Patent Application EP 391, 22, nail varnishes containing an aqueous dispersion of a polyurethane and/or of a polyurethane copolymer have also been described.

The use of these resins does not, however, enable compositions possessing good cosmetic properties to be procured, as a result, in particular, of a lack of staying power.

SUMMARY OF THE INVENTION

The present invention relates to polyurethanes and a process for preparing them. These polyester polyurethanes contain units corresponding to the following formulae (I) and (II):

$$\left[O-R_2-O-\left(\underset{O}{\overset{\parallel}{C}}-R_1-\underset{O}{\overset{\parallel}{C}}-O-R_2-O\right)_n \underset{O}{\overset{\parallel}{C}}-NH-R-NH-\underset{O}{\overset{\parallel}{C}}\right] \quad (I)$$

and $$\left[O-A-O-\underset{O}{\overset{\parallel}{C}}-NH-R-NH-\underset{O}{\overset{\parallel}{C}}\right] \quad (II)$$

The polyester polyurethanes according to the present invention form pseudolatices and may be utilized as film-forming resin in cosmetic compositions.

It has now been found that, surprisingly and unexpectedly, a new family of polyester polyurethanes not only possess good film-forming properties, but also enable films possessing both great rigidity and excellent resistance to removal by water and detergents to be obtained.

It has been possible to obtain these excellent properties as a result of the particular choice of α, ω-dihydroxy polyester participating in the synthesis of the polyester polyurethanes according to the invention.

The polyester polyurethanes according to the invention make it possible to prepare pseudolatices which also have very good staying power and which, furthermore, are especially stable without the use of additional surfactants, in as much as they contain, in addition, ionic functions.

DESCRIPTION OF THE PREFERRED EMBODIMENTS

The subject of the present invention is, as a new industrial product, a polyester polyurethane containing units corresponding to the following formulae (I) and (II):

$$\left[O-R_2-O-\left(\underset{O}{\overset{\parallel}{C}}-R_1-\underset{O}{\overset{\parallel}{C}}-O-R_2-O\right)_n \underset{O}{\overset{\parallel}{C}}-NH-R-NH-\underset{O}{\overset{\parallel}{C}}\right] \quad (I)$$

in which:

R represents an alkylene or cycloalkylene radical or a bivalent aromatic radical having from 6 to 15 carbon atoms, n represents an integer such that the molecular weight of the recurring unit is between 400 and 5,000, $R_1$ represents a bivalent radical chosen from the group consisting of;

(i) $-(CH_2)_m-$, m being an integer between 2 and 12, and (ii)

the movable bond being in the ortho, meta or para position,

R2 represents a bivalent radical chosen from the group consisting of:

$$\left[-CH_2-\underset{\underset{CH_3}{|}}{\overset{\overset{CH_3}{|}}{C}}-\underset{O}{\overset{\parallel}{C}}-O\right]_p-CH-\underset{\underset{R_4}{|}}{\overset{\overset{R_5}{|}}{C}}-CH_2- \quad (a)$$

$R_3$ representing a hydrogen atom or a branched alkyl radical having from 1 to 3 carbon atoms, $R_4$ representing a hydrogen atom or a linear or branched alkyl radical having from 1 to 4 carbon atoms, $R_5$ representing a linear or branched alkyl radical having from 1 to 4 carbon atoms, and p being 0 or 1, $-CH_2-\text{(cyclohexyl)}-CH_2-$, (b)

-continued

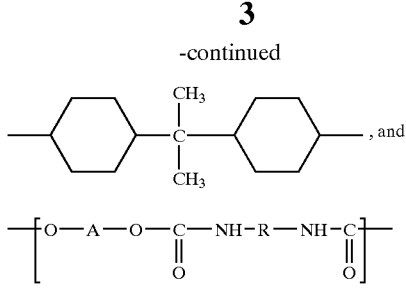, and (c)

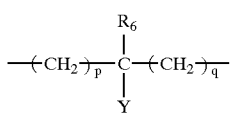 (II)

in which:

R is as defined above for the units of formula (I),

A represents an alkylene radical having from 2 to 20 carbon atoms, substituted with a carboxylic or sulphonic acid function, in salified or unsalified form, or interrupted by a tertiary nitrogen atom, the mole ratio between the units (II) and (I) being between 1:1 and 10:1, and preferably between 1:1 and 5:1.

The bivalent radical R of the unit of formula (I) is preferably chosen from the group consisting of hexamethylene, 4,4'-biphenylenemethane, 2,4-and/or 2,6-tolylene, 1,5-naphthylene, p-phenylene and 4,4'-methylenebis (cyclohexyl) radicals and the bivalent radical derived from isophorone.

The bivalent radical A of the unit of formula (II) is preferably chosen from the group consisting of:

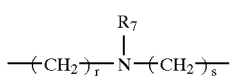 (1)

$R_6$ representing a linear or branched alkyl radical having from 1 to 3 carbon atoms, Y representing a carboxylic acid or sulphonic acid group or a salt thereof, and t and q, which may be identical or different, representing an integer between 1 and 5, $-(CH_2)_r-N(R_7)-(CH_2)_s-$ (2)

$R_7$ representing a linear or branched alkyl radical having from 1 to 4 carbon atoms, and r and s, which may be identical or different, representing an integer between 1 and 10.

The polyester polyurethanes according to the invention can, in addition, contain units corresponding to the following formula (III):

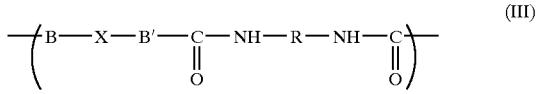 (III)

in which:

R is as defined above for the units of formula (I),

B and B', which may be identical or different, represent —O— or —NH—, it not being possible for B and B' simultaneously to represent —O—, and X represents an alkylene or cycloalkylene radical having from 2 to 12 carbon atoms or a bivalent aromatic radical having from 6 to 12 carbon atoms, the said unit being present in a proportion such that the mole ratio of the sum of the units of formulae (II) and (III) to the units of formula (I) is an integer between 1 and 10, and preferably between 1 and 5.

The molecular weight of the polyester polyurethanes according to the invention, measured by steric exclusion chromatography, is generally between 4,000 and 500,000, and preferably between 6,000 and 200,000.

The subject of the present invention is also the process for preparing said polyester polyurethanes. This process consists in reacting, in an organic solvent, an α, w-dihydroxy polyester corresponding to the following formula (IV):

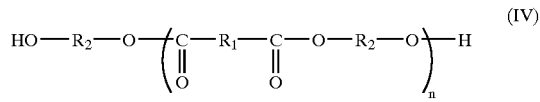 (IV)

in which:

$R_1$, $R_2$ and n are as defined above for the units of formula (I), with an excess of a diisocyanate corresponding to the following formula (V):

$O=C=N-R-N=C=O$ (V)

in which R is as defined above for the units of formula (I), and then in coupling the chains of the polyester polyurethane obtained above with a diol corresponding to the following formula (VI):

HO—A—OH (VI)

in which:

A is as defined above for the units of formula (II), at a temperature of between 40 and 100° C. in the presence of a tin salt as catalyst.

The organic solvent used in the process according to the invention is preferably chosen from the group consisting of acetone, methyl ethyl ketone, tetrahydrofuran and 1,2-dichloroethane, these solvents being inert with respect to isocyanate groups.

The tin salt is preferably chosen from tin 2-ethylhexanoate and dibutyltin dilaurate.

The α,ω-dihydroxy polyester of formula (IV) used as starting material in the synthesis of the polyester polyurethanes according to the invention preferably has a molecular weight of between 400 and 5,000.

Among especially preferred α,ω-dihydroxy polyesters of formula (IV), there may be mentioned that in which $R_2$ represents a bivalent radical of formula:

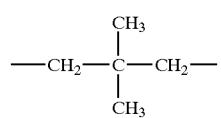

and $R_1$ represents —$(CH_2)_3$— or a p-phenylene radical.

The diisocyanate of formula (V) used in the process according to the invention is preferably chosen from the group consisting of diphenylmethane 4,4'-diisocyanate and dicyclqhexylmethane 4,4'-diisocyanate (or dicyclohexylmethylene 4,4'-diisocyanate).

The diol of formula (VI) used in the process according to invention is preferably chosen from the group consisting of dimethylolpropionic acid and N-methyldiethanolamine.

According to a particular embodiment of the process according to the invention, a coupler corresponding to the following formula (VII):

H—B—X—B'—H (VII)

in which:

B, B' and X are as defined above for the units of formula (III), is reacted in addition.

Preferably, the coupler is chosen from the group consisting of 1,3-diaminopropane and ethanolamine.

The polyester polyurethane obtained according to the above process is in non crosslinked form and can optionally be purified, for example by precipitation in a non-polar solvent such as cyclohexane.

The subject of the present invention is also, as a new industrial product, a stable pseudolatex consisting of particles of non crosslinked polyester polyurethane as defined and obtained above, neutralized using a neutralizing agent which can be either an inorganic or organic base when the radical A of the units of formula (II) is substituted with a carboxylic or sulphonic acid function, or an inorganic or organic acid when the radical A of the units of formula (II) is interrupted by a tertiary nitrogen atom, to a degree of neutralization of between 20 and 100%, the average diameter of the particles being between 5 and 300 nm.

According to the invention, the term "pseudolatex" is understood to mean a suspension consisting of generally spherical particles of the polyester polyurethane, these being obtained by dispersion of the polyester polyurethane in a suitable aqueous phase. The term "pseudolatex" should not be confused with the term "latex" or "synthetic latex", which is also a suspension consisting of particles of a polymer, but in which the said particles are obtained directly by polymerization of one or more monomers in a suitable aqueous phase.

The pseudolatices according to the invention are obtained according to known methods of preparation of pseudolatices, subject, however, to certain features which will be mentioned below.

The conventional process for preparing pseudolatices consists in dissolving a water-insoluble polymer in an organic solvent which is soluble or partially soluble in water, in dispersing the dispersion thereby obtained in water while stirring and removing the organic solvent by evaporation under vacuum, which leads to a suspension consisting of particles of the polymer whose size is generally less than one micrometer.

According to this general process, the use of a surfactant, a mixture of surfactants or a protective colloidal polymer, or alternatively of a surfactants/protective colloidal polymer mixture, is essential for the purpose of obtaining good stabilization of the particles.

In contrast, the polyester polyurethanes according to the invention, containing partially or completely neutralized ionic functions, enable especially stable pseudolatices to be obtained in the absence of a hydrophilic stabilizer, a surfactant or a protective colloid.

It is self-evident that the acidic or basic nature of the neutralizing agent which it will be appropriate to use in order to neutralize the polyester polyurethane will be dependent on the nature of the ionic functions borne by the said polyester polyurethane.

When the polyester polyurethane contains a carboxylic or sulphonic acid function, the neutralizing agent can be an inorganic base such as sodium hydroxide, potassium hydroxide or ammonia solution, or an organic base such as an amino alcohol chosen from 2-amino-2-methyl-1-propanol (AMP), triethanolamine, triisopropanolamine (TIPA), monoethanolamine, diethanolamine, tris(2-hydroxy-1-propyl)amine, 2-amino-2-methyl-1,3-propanediol (AMPD) and 2-amino-2-hydroxymethyl-1,3-propanediol, or alternatively a diamine such as lysine.

When the polyester polyurethane contains a tertiary amine function, the neutralizing agent can be an inorganic acid such as hydrochloric acid or an organic acid such as lactic acid, glycolic acid or mandelic acid.

The neutralization may be carried either in situ in the solution of the polyester polyurethane in the organic solvent, by adding the specified amount of neutralizing agent, or during the preparation of the emulsion, the neutralizing agent then being in the aqueous phase of the emulsion. The organic solvent used must be a volatile solvent or a mixture of such solvents possessing a boiling point below that of water, and be miscible or partially miscible with water.

The organic solvent as defined above is preferably chosen from acetone, methyl ethyl ketone, tetrahydrofuran, methyl acetate, ethyl acetate, isopropanol and ethanol.

After the completely or partially neutralized polyester polyurethane has been obtained in the organic solvent, an emulsion is then prepared by pouring into the organic solution obtained, while stirring, a suitable amount of water optionally containing an antifoaming agent whose role will be to facilitate the subsequent evaporation of the organic phase.

According to a variant of the process as defined above, the neutralization of the ionic functions of the polyester polyurethane, dissolved in an organic solvent, may be carried out during the formation of the emulsion by pouring in an aqueous solution containing the requisite amount of the neutralizing agent.

During the formation of the emulsion, the stirring is preferably carried out using a shearing disperser of the Moritz or Ultra Turrax or Raineri type, equipped with deflocculating blades.

The emulsion thereby obtained is especially stable without it being necessary to employ a surfactant, inasmuch as the ionic groups of the polyester polyurethane place themselves at the interface with the water and protect the droplets from coalescence by electrostatic repulsion.

After formation of the emulsion at a temperature between room temperature and 70° C. approximately, the organic solvent is then evaporated off under reduced pressure until it has been removed completely, the evaporation preferably being carried out under gentle heating.

A pseudolatex, that is to say an aqueous dispersion of particles of the film-forming polyester is polyurethane, is thereby obtained, which pseudolatex is free from any surfactant or from any other hydrophilic stabilizer while being very stable.

The average size of the particles of the pseudolatex and their polydispersity may be adjusted by varying, during the preparation of the said pseudolatex, the respective proportions between the polyester polyurethane, the organic solvent and water, thus modifying, in particular, the viscosity of the said pseudolatex and the sheen of the film obtained after evaporation. The average size of the particles also depends on the degree of neutralization and on the nature of the neutralizing agent.

According to a preferred embodiment of the pseudolatices according to the invention, the average size of the particles is between 10 and 250 nm.

The size polydispersity of the particles, measured by quasi-elastic light scattering, is generally less than 0.5 and preferably between 0.05 and 0.4.

The polyester polyurethanes according to the invention may be plasticized in order to improve film formation at room temperature. The plasticizing may he carried out by mixing the pseudolatex of polyester polyurethane according to the invention with an aqueous dispersion of a polyether polyurethane or polyester polyurethane having elastomeric character, these dispersions being of the same ionic nature as the polyester polyurethane according to the invention.

As dispersions of polyether polyurethanes having elastomeric character and of anionic nature, those sold under the names "Sancure 861" or "Sancure 878" by the company Sanncor, or under the name "Neorez-R970" by the company ICI, may be mentioned in particular.

As dispersions of polyester polyurethanes having elastomeric character and of ionic nature, that sold under the name "Neorez-R974" by the company ICI may be mentioned in particular.

The plasticizing may also be carried out using non-polymeric traditional plasticizers. It is then necessary for the plasticizer to be a good solvent for the polyester polyurethane according to the invention, and preferably to be insoluble in water. Among hydrophobic plasticizers, there may be mentioned, in particular:

diethyl, dibutyl and di-2-ethylhexyl phthalates and adipates, diethyl and dibutyl tartrates, diethyl, dibutyl and di-2-ethylhexyl phosphates, propylene glycol derivatives chosen from propylene glycol phenyl ether, propylene glycol diacetate, dipropylene glycol butyl ether and tripropylene glycol butyl ether, glycerol esters such as glyceryl triacetate (triacetin).

the propylene glycol monophenyl ether sold under the name "Dowanol PPH" by the company Dow Chemical, and the dipropylene glycol n-butyl ether sold under the name "dowanol DPnB" by the Company Dow Chemical.

The plasticizer may be incorporated in a proportion ranging from 5 to 50% by weight relative to the total weight of the aqueous dispersion either after the production of the pseudolatex, or during the production of the pseudolatex when the emulsion is being formed, the plasticizer then being incorporated in the organic phase of the emulsion.

The subject of the invention is also a water-based cosmetic composition comprising as film-forming resin and preferably as the sole film-forming resin, the neutralized non crosslinked polyester polyurethane in the form of particles in an aqueous dispersion (pseudolatex) as defined above.

The proportion of pseudolatex in the cosmetic compositions is generally between 0.5 and 30%, and preferably between 1 and 25%, by weight relative to the total weight of the composition.

The cosmetic compositions according to the invention can take various forms, for example the form of make-up products for the nails or eyelashes such as nail varnishes or mascaras, and skin care products such as face packs or serums.

The compositions according to the invention can also take the form of hair care products such as styling shampoos, hair-end treatment lotions, hair lacquers and styling gels.

The compositions according to the invention can, in addition, contain UV-A or UV-B or broad-band sunscreen agents, and be used as antisun products.

The compositions according to the invention can contain, moreover, conventional cosmetic adjuvants chosen from fats, organic solvents, silicones, thickening agents, emollients, antifoaming agents, hydrating agents, humectants, nail hardeners, anionic, nonionic or amphoteric polymers or mixes thereof, antiperspirants, alkalinizing agents, colorants, pigments and propellent agents when the compositions take the form of an aerosol.

More specifically, as a fat, it is possible to use an oil or a wax or mixtures thereof, fatty acids, fatty alcohols, fatty acid esters such as $C_6$ to $C_{18}$ fatty acid triglycerides, petroleum jelly, paraffin, lanolin or hydrogenated or acetylated lanolin.

Among oils, mineral, animal and vegetable oils or synthetic oils may be mentioned, and in particular liquid petrolatum and paraffin, castor, jojoba and sesame oils, as well as Silicone oils and gums and isoparaffins.

Among animal, fossil, vegetable, mineral or synthetic waxes, beeswax, carob wax, candelilla wax, ozokerite and microcrystalline waxes may be mentioned, as well as silicone waxes and resins.

Among thickening agents, there may be mentioned:

cellulose derivatives such as hydroxyethylcellulose, methylcellulose, hydroxypropylcellulose and carboxymethylcellulose. Among these, the gums sold under the name "Cellosize QP 4400H" by the company Amerchol may be mentioned in particular, carob gum, guar gum, the quaternized guar gum sold under the name "Jaguar C-13-S" by the company Meyhall, hydroxypropylguar gum, xanthan gum, crosslinked polyacrylic acids such as those sold under the name "Carbopol", by the company Goodrich, crosslinked acrylic acid/($C_{10}$/C30) alkyl acrylate copolymers such as those sold under the names "Pemulen $TR_1$" and "Pemulen $TR_2$" by the company Goodrich, the poly [glyceryl (meth) acrylate] polymers sold under the names "Hispagel" or "Lubragel" by the companies Hispano Quimica or Guardian, polyvinylpyrrolidone, polyvinyl alcohol, the crosslinked acrylamide polymers and copolymers sold under the names "PAS 5161" or "Bozepol C" by the company Hoechst, "Sepigel 305" by the company Seppic or "salcare SC92" by the company Allied Colloid, or alternatively the crosslinked methacryloyloxyethyltrimethylammonium chloride homopolymers sold under the name "Salcare SC95" by the company Allied Colloid.

The compositions according to the invention find application most especially in nail care and treatment.

Thus, they can constitute a base coat for the subsequent application, after drying, of a traditional coloured nail varnish. The base coat thus protects the nail from the potentially damaging effect of the nail varnish solvent mixture, and prevents, moreover, the keratin of the nail from being coloured through the effect of the pigments. This base coat makes it possible, moreover, to improve the adhesion of the nail varnish, and can contain various active agents for nail care in so far as they are soluble in water or readily dispersable.

The advantage of using, according to this embodiment, a base coat of a composition according to the invention enables the nail varnish to be made strippable by simultaneous removal of the base coat and the nail varnish layer.

The compositions according to the invention can also constitute a top coat after application and drying of a traditional coloured nail varnish. This upper coat provides sheen and better mechanical resistance.

According to an especially preferred form, the compositions according to the invention take the form of coloured aqueous nail varnish.

These nail varnishes contain at least one pseudolatex as defined above in a proportion of 1 to 25% by weight, at least one thickening agent in a proportion of 0.01 to 5% and preferably of 0.1 to 1% by weight, at least one pigment in a proportion of less than 3% and preferably of between 0.5 and 2% by weight and at least one wetting agent in a proportion of 0.1 to 1% by weight, the remainder consisting essentially of water.

Several examples of preparations of polyester polyurethanes, and also of pseudolatices and cosmetic compositions containing them, will now be given by way of illustration of the invention.

Process for preparing α,ω-dihydroxy Polyesters

EXAMPLE A

Preparation of an α,ω-dihydroxy polyester with a 50:50 molar content of 2,2-dimethyl-1,3-propanediol terephthalatesebacate 274.6 g (2.64 mol) of 2,2-dimethyl-1,3-propanediol and 138 g (0.6 mol) of previously melted dimethyl sebacate are introduced into a 500-ml reactor, and the mixture is then heated with stirring until a clear medium is obtained, that is to say to approximately 100° C. 116.4 g (0.6 mol) of dimethyl terephthalate are then added, the mixture is thereafter heated to 150° C. and 1.6 g (0.3% by weight relative to the total weight of the reactants) of zinc acetate dihydrate are then added.

The temperature of the reaction medium is maintained at 150° C. for 3 hours in order to remove the methanol formed by transesterification, then raised to 200° C. over 45 minutes and maintained for 3 hours.

The mixture is then allowed to return to room temperature while stirring is decreased. Once the temperature reaches 50° C., 300 ml of 1,2-dichloroethane are then added.

The solution is then diluted in 1.7 l of 1,2-dichloroethane and thereafter purified by washing with water.

The organic phase is then dried over anhydrous sodium sulphate and thereafter, following filtration, the extraction solvent is removed by evaporation under vacuum.

300 g of expected α,ω-dihydroxy polyester are thereby obtained, which product takes the form of a paste at room temperature.

Characteristics of the α,ω-dihyroxy polyester obtained:

Hydroxyl value: 190

Molecular weight (determined from the hydroxyl value): 560 IR and RMN: in agreement with the expected data.

EXAMPLES B to D

According to the same process as described in Example A, the α,ω-dihydroxy polyesters of Table I below were prepared:

TABLE I

| Ex-ample | Amounts of reactants | | | Characteristics of the dihydroxy polyester obtained | |
|---|---|---|---|---|---|
| | Dimethyl terephthalate | Dimethyl sebacate | 2,2-Dimethyl-1,3-propanediol | OH value | Molecular weight |
| B | 232.8 g (1.2 mol) | | 274.6 g (2.64 mol) | 190 | 590 |
| C | | 276 g (1.2 mol) | 274.6 g (2.64 mol) | 185 | 605 |
| D | 56.2 g (0.3 mol) | 207 g (0.9 mol) | 274.6 g (2.64 mol) | 195 | 570 |

Process for preparing the polyester Polyurethanes

EXAMPLE 1

Preparation of a non crosslinked polyester polyurethane from the prepolymer of Example A 78.6 g (0.3 mol) of dicyclohexylmethane diisocyanate and 150 g of 1,2-dichloroethane are introduced under nitrogen into a 1—1 reactor. The mixture is brought to reflux over 30 minutes under a stream of nitrogen, and then left stirring for 30 minutes at 80° C.

83.2 g (0.15 mol) of the α,ω-dihydroxy polyester of Example A, previously dissolved in 200 g of 1,2-dichloroethane, are then added dropwise over 15 minutes and at 80° C.

After 3 hours, 4.8 g (0.075 mol) of ethanolamine dissolved in 50 g of 1,2-dichloroethane are added, and reaction is allowed to proceed for 1 hour. 10.05 g (0.075 mol) of dimethylolpropionic acid previously dissolved in 30 g of dimethylformamide are then introduced, followed by 0.45 g of tin 2-ethylhexanoate.

After 12 hours at 80° C., the absence of residual isocyanate groups is checked by infrared. If the consumption of dicyclohexylmethane diisocyanate is not complete, 100 g of ethanol are added to the mixture and reaction is allowed to proceed for 2 hours under reflux.

After cooling, the solution of polyester/polyurethane is purified by precipitation in cyclohexane, and the precipitate is dried under vacuum in an oven at 50° C.

Characteristics of the polyester polyurethane obtained:

Yield: 91%

Potentiometric assay of acid groups: 6.4% by weight (theory: 5.7%)

Molecular weight (steric exclusion chromatography eluent: tetrahydrofuran): 9000

EXAMPLES 2 to 10

According to the same process as described in Example 1, non crosslinked polyester polyurethanes of Table II below were prepared:

TABLE II

| | | | | | Characteristics of the polyester polyurethane | | |
|---|---|---|---|---|---|---|---|
| Example | Nature of the prepolymer (Amount) | Nature of the diisocyanate (Amount) | Nature of the coupler (Amount) | Reaction solvent | Yield % by weight | % by weight theoretical acid groups | % by weight acid groups found |
| 2 | Example A (1 mol) | DCMD (2 mol) | DMPA (1 mol) | THF | 91 | 6.7 | 11.7 |
| 3 | Example A (1 mol) | DPMD (2 mol) | DMPA (1 mol) | THF | 89 | 10 | 11.8 |

TABLE II-continued

| Example | Nature of the prepolymer (Amount) | Nature of the diisocyanate (Amount) | Nature of the coupler (Amount) | | Reaction solvent | Yield % by weight | Characteristics of the polyester polyurethane | |
|---|---|---|---|---|---|---|---|---|
| | | | | | | | % by weight theoretical acid groups | % by weight acid groups found |
| 4 | Example A (1 mol) | DCMD (3 mol) | DMPA (2 mol) | | THF | 91 | 15.6 | 16.9 |
| 5 | Example D (1 mol) | DCMD (2 mol) | DMPA (0.5 mol) | Ethanolamine (0.5 mol) | THF | 92 | 5.6 | 6.4 |
| 6 | Example C (1 mol) | DPMD (2 mol) | DMPA (0.5 mol) | Ethanolamine (0.5 mol) | 1,2-dichloroethane | 81 | 5.5 | 6.8 |
| 7 | Example B (1 mol) | DCMD (2 mol) | DMPA (0.5 mol) | Ethanolamine (0.5 mol) | 1,2-dichloroethane | 80 | 5.5 | 6.8 |
| 8 | Example B (1 mol) | DCMD (2 mol) | DMPA (1 mol) | | 1,2-dichloroethane | 70 | 10.1 | 11.4 |
| 9 | Example A (1 mol) | DCMD (2 mol) | N-MDEA (1 mol) | | THF | 82 | 45.5 | 45.3 |
| 10 | Example A (1 mol) | DCMD (3 mol) | N-MDEA (2 mol) | | THF | 86 | 69.5 | 70 |

DPMD = diphenylmethane diisocyanate
DCMD = dicyclohexylmethane diisocyanate
DMPA = dimethylolpropionic acid
THP = tetrahydrofuran
N-MDEA = N-methyldiethanolamine

EXAMPLE 11

According to the same process as described in Example 1, the following reactants are reacted:

dicyclohexylmethane diisocyanate: 78.6 g (0.3 mol)

α,ω-dihydroxy polyester of Example A: 83.2 g (0.15 mol)

After 3 hours, the mixture is cooled to 5° C., and 3.3 g (0.045 mol) of 1,3-diaminopropane previously dissolved in 50 g of tetrahydrofuran are then added. After 1 hour with stirring, the mixture is heated to 80° C. and 14.07 g (0.105 mol) of dimethylolpropionic acid and 0.45 g of tin 2-ethylhexanoate are added.

After 12 hours at 80° C., the absence of residual isocyanate groups is checked by infrared. It the consumption of dicyclohexylmethane diisocyanate is not complete, 100 g of ethanol are added to the mixture and reaction is allowed to proceed for 2 hours under reflux.

After cooling, the solution of the polyester polyurethane is purified by precipitation in cyclohexane, and the precipitate is then dried under vacuum in an oven at 50° C.

Characteristics of the polyester polyurethane obtained:
Yield: 93%
Potentiometric assay of acid groups: 8.5% by weight (theory: 7.2%).

Preparation of pseudolatices of the polyester polyurethanes

EXAMPLE I

Preparation of the pseudolatex of the polyester polyurethane of Example 1

At room temperature, 10 g of the polyester polyurethane obtained in Example 1 are dissolved in 100 g of tetrahydrofuran, the mixture is stirred with a Moritz type stirrer, a mixture of 45 g of water and 0.41 g of 2-amino-2-methylpropanol is then introduced gradually and the resulting mixture is stirred for 15 minutes.

The emulsion thereby obtained is then concentrated in a rotary evaporator under partial vacuum and at a temperature below 45° C. until the tetrahydrofuran has been completely removed.

The pseudolatex of polyester polyurethane thereby obtained is stable.

Characteristics of the pseudolatex obtained:

Degree of neutralization: 100%

Concentration of polymers in the pseudolatex: 27%

Average particle size (measured by quasi-elastic light scattering using a Coultronix company Coulter N4): 50 nm Polydispersity of the particles: 0.3

EXAMPLES II to XVII

According to the same process as described in Example I, the pseudolatices of polyester polyurethanes of Table III below were prepared:

TABLE III

| Example | Nature of the polyester polyurethane | Nature of the neutralizing agent and degree of neutralization | | Final dry extract % | Average particle size nm | Particle size polydispersity |
|---|---|---|---|---|---|---|
| II | Example 2 | NaOH | 100% | 30.4 | 50 | 0.23 |
| III | Example 2 | AMP | 100% | 24 | 45 | 0.25 |
| IV | Example 2 | NaOH + L-lysine | 50% 25% | 27 | 110 | 0.30 |
| V | Example 3 | AMP | 100% | 23 | 30 | 0.23 |
| VI | Example 4 | AMP | 60% | 30 | 30 | 0.27 |
| VII | Example 4 | NaOH + L-lysine | 50% 25% | 30 | 120 | 0.23 |
| VIII | Example 5 | AMP | 100% | 23 | 50 | 0.33 |
| IX | Bxample 6 | AMP | 100% | 25 | 45 | 0.30 |
| X | Example 7 | AMP | 100% | 23 | 25 | 0.28 |
| XI | Example 8 | AMP | 100% | 30 | 30 | 0.25 |
| XII | Example 8 | NaOH + L-lysine | 50% 25% | 25 | 100 | 0.25 |
| XIII | Example 9 | HCl | 80% | 25 | 30 | <0.2 |
| XIV | Example 9 plasticized* | HCl | 80% | 25 | 30 | 0.30 |
| XV | Example 10 | HCl | 70% | 25 | 25 | <0.3 |
| XVI | Example 11 | AMP | 100% | 23 | 40 | 0.25 |
| XVII | Example 11 | NaOH + L-lysine | 50% 25% | 22 | 130 | 0.30 |

*plasticizing is carried out with 5% of propylene glycol phenyl ether which has been introduced into the organic phase before production of the emulsion.

EXAMPLES OF COMPOSITIONS

In the following examples, the letters "AS" mean "active substance" when the product used, commercial or otherwise, is in the form of a solution or dispersion in a solvent.

EXAMPLE 1

Nail varnish

This nail varnish is prepared by mixing the following ingredients:

| | |
|---|---|
| Pseudolatex of Example I | 24.88 g (AS) |
| Dipropylene glycol n-butyl ether sold under the name "dowanol DPnB" by the company Dow Chemical | 3.23 g |
| Urethane nonionic associative thickener sold under the name "SER AD FX 1100" by the company Servo | 0.3 g |
| Pigments | 1.0 g |
| Fluorinated surfactant sold under the name "forafac 1157" by the company Atochem | 0.1 g |
| Water qs | 100 g |

The nail varnish obtained is very resistant to water: the film is intact after 1 hour's stirring in water.

The film hardness is measured by the Persoz pendulum method, at 30° C. and at 50% relative humidity, after the said film of thickness 300 μm has been allowed to dry on a glass plate in a chamber at 30° C. and at 50% relative humidity for 24 hours.

Film hardness: 63.3+/±2.5 seconds.

The measured hardness is very satisfactory, the film adheres correctly to the keratin of the nail without flaking. It is not tacky and is scratch-resistant.

The varnish obtained according to the invention is readily applied to the nail and possesses sheen and satisfactory hold.

EXAMPLE 2

Nail varnish

This nail varnish is prepared by mixing the following ingredients:

| | |
|---|---|
| Pseudolatex of Example I | 22.6 g (AS) |
| Propylene glycol monophenyl ether sold under the name "Dowanol PPH" by the company Dow Chemical | 2.49 g |
| Urethane nonionic associative thickener sold under the name "SER AD FX 1100" by the company Servo | 0.3 g |
| Pigments | 1.0 g |
| Fluorinated surfactant sold under the name "Forafac 1157" by the company Atochem | 0.1 g |
| Water qs | 100 g |

The nail varnish obtained is very resistant to water: the film is intact after 1 hour's stirring in water.

Film hardness (30° C.–50% relative humidity): 77.0±5.4 seconds.

EXAMPLE 3

Nail varnish

This nail varnish is prepared by mixing the following ingredients:

| | |
|---|---|
| Pseudolatex of Example IX | 20.65 g (AS) |
| Urethane nonionic associative thickener sold under the name "SER AD FX 1100" by the company Servo | 0.3 g |
| Pigments | 1.0 g |
| Preservatives | 0.05 g |
| Water qs | 100 g |

Film hardness (30° C.–50% relative humidity): 89.4±1.4 seconds.

This varnish is applied readily to the surface of the nails. The film obtained possesses satisfactory sheen and is shock-resistant.

The resistance of the film to water is very satisfactory.

EXAMPLE 4

Nail varnish

This nail varnish is prepared by mixing the following ingredients:

| | |
|---|---|
| Pseudolatex of Example XIII | 20.7 g (AS) |
| Propylene glycol monophenyl ether sold under the name "Dowanol PPH" by the company Dow Chemical | 1.07 g |
| Urethane nonionic associative thickener sold under the name "SER AD FX 1100" by the company Servo | 0.5 g |
| Pigments | 1.0 g |
| Preservatives | 0.045 g |
| Fluorinated surfactant sold under the name "Forafac 1157" by the company Atochem | 0.3 g |
| Water qs | 100 g |

This varnish is applied readily to the nails and possesses satisfactory sheen and hardness. The nail varnish obtained is very resistant to water.

Film hardness (30° C.–50% relative humidity): 104.90±2.5 seconds.

EXAMPLE 5

Nail varnish

This nail varnish is prepared by mixing the following ingredients:

| | |
|---|---|
| Pseudolatex of Example XV | 20.7 g (AS) |
| Urethane nonionic associative thickener sold under the name "SER AD FX 1100" by the company Servo | 0.5 g |
| Pigments | 1.0 g |
| Preservatives | 0.045 g |
| Fluorinated surfactant sold under the name "Forafac 1157" by the company Atochem | 0.3 g |
| Water qs | 100 g |

This nail varnish possesses very good resistance to water. The film obtained after drying is shock- and scratch-resistant.

Film hardness (30° C.–50% relative humidity): 232.3±4.7 seconds.

EXAMPLE 6

Mascara

| Phase A: | |
|---|---|
| Triethanolamine stearate | 11.8 g |
| Beeswax | 5 g |
| Carnauba wax | 3 g |
| Paraffin | 1 g |
| Phase B: | |
| Black iron oxide | 5 g |
| Phase C: | |
| Gum arabic | 2 g |
| Hydroxyethylcellulose sold under the name "Cellosize QP" by the company Amerchol | 1.2 g |
| Phase D: | |
| Pseudolatex of Example I plasticized with 11% of propylene glycol phenyl ether sold under the name "Dowanol PPH" by the company Dow Chemical | 5 g |
| Preservatives qs | |
| Water qs | 100 g |

This mascara is obtained by bringing the ingredients of Phase A to 85° C., to which Phase B is added, and the mixture is stirred using a turbo-mixer.

The water of preparation is then brought to the boil and the preservatives are added, followed, at 85° C., by the ingredients of Phase C.

The aqueous phase obtained (85° C.) is then added to Phase A: (80° C.) with stirring using a turbo-mixer (emulsification), followed by the pseudolatex of Phase D added last at 30° C., and the mixture is stirred using a paddle.

EXAMPLE 7

Mascara

This mascara, having the following composition, is prepared according to the same procedure as that described in Example 6:

| Phase A: | |
|---|---|
| Triethanolamine stearate | 12 g |
| Beeswax | 8 g |
| Carnauba wax | 3 g |
| Paraffin | 2 g |
| Phase B: | |
| Black iron oxide | 5 g |
| Phase C: | |
| Gum arabic | 2.5 g |
| Hydroxyethylcellulose sold under the name "Cellosize QP" by the company Amerchol | 1.5 g |
| Keratin hydrolysate sold under the name "Kerasol" by the company Croda | 1 g |
| Phase D: | |
| Pseudolatex of Example I, plasticized with 13% of dipropylene glycol n-butyl ether sold under the name "Dowanol DPnB" by the company Dow Chemical | 4 g |
| Preservatives qs | |
| Water qs | 100 g |

EXAMPLE 8

Mascara

This mascara, having the following composition, is prepared according to the same procedure as that described in Example 6:

| Phase A: | |
|---|---|
| Triethanolamine stearate | 11 g |
| Beeswax | 10 g |
| Carnauba wax | 2 g |
| Paraffin | 1 g |
| Phase B: | |
| Black iron oxide | 6 g |
| Phase C: | |
| Gum arabic | 0.8 g |
| Hydroxyethylcellulose sold under the name "Cellosize QP" by the company Amerchol | 2 g |
| Phase D: | |
| Pseudolatex of Example IX | 6 g |
| Preservatives qs | |
| Water qs | 100 g |

EXAMPLE 9

Mascara

This mascara, having the following composition, is prepared according to the same procedure as that described in Example 6:

| Phase A: | |
|---|---|
| Glyceryl stearate | 3 g |
| Mixture of esters of lauric acid and sorbitol and of lauric acid and oxyethylenated sorbitol containing 20 mol of ethylene oxide, sold under the name "Tween 20" by the company ICI | 3.7 g |
| Monoesters of stearic acid and sorbitan, sold under the name "Span 60" by the company ICI | 5.6 g |
| Beeswax | 6 g |
| Carnauba wax | 1.8 g |
| Paraffin | 7.8 g |
| Phase B: | |
| Black iron oxide | 4.5 g |
| Phase C: | |
| Hydroxyethylcellulose sold under the name "Cellosize QP" by the company Amerchol | 1.5 g |
| Phase D: | |
| Pseudolatex of Example XV | 2 g |
| Preservatives qs | |
| Water qs | 100 g |

EXAMPLE 10

Eyeliner

| Phase A: | |
|---|---|
| Black iron oxide | 12 g |
| Phase B: | |
| Propylene glycol | 4 g |
| Hydroxyethylcellulose sold under the name "Cellosize QP" by the company Amerchol | 0.1 g |
| Laponite | 0.5 g |
| Phase C: | |
| Pseudolatex of Example I, plasticized with 11% of propylene glycol phenyl ether sold under the name "Dowanol PPH" by the company Dow Chemical | 5 g |
| Preservatives qs | |
| Water qs | 100 g |

This eyeliner is obtained by mixing the ingredients of Phase B with water brought to 70° C. in which the preservatives have been dissolved.

The black iron oxide of Phase A is then added, the ingredients are mixed using a turbo-mixer at room temperature and the pseudolatex of Phase C is then added with stirring.

EXAMPLE 11

Hair style shading lotion

This lotion is prepared by mixing the following ingredients:

| Pseudolatex of Example I | 5 g (AS) |
|---|---|
| Colorants qs | |
| Preservatives qs | |
| Perfumes qs | |
| Water qs | 100 g |

The shaping lotion obtained is applied after shampooing, and imparts good shape-retention to the hair style.

EXAMPLE 12

Hair style shaping lotion

This lotion is prepared by mixing the following ingredients:

| Pseudolatex of Example I | 1 g (AS) |
|---|---|
| Propylene glycol monophenyl ether sold under the name "Dowanol PPH" by the company Dow Chemical | 0.11 g |
| Colorants qs | |
| Preservatives qs | |
| Perfumes qs | |
| Water qs | 100 g |

EXAMPLE 13

Hair styling lotion in a pump bottle

This lotion is prepared by mixing the following ingredients:

| Pseudolatex of Example I | 3 g (AS) |
|---|---|
| Dipropylene glycol n-butyl ether sold under the name "Dowanol DPnB" by the company Dow Chemical | 0.39 g |
| Colorants qs | |
| Preservatives qs | |
| Perfumes qs | |
| Water qs | 100 g |

The lotion obtained is sprayed onto the hair after shampooing, and imparts good shape-retention to the hair style.

EXAMPLE 14

Hair style shaping lotion

This lotion is prepared by mixing the following ingredients:

| Pseudolatex of Example IX | 4 q (AS) |
|---|---|
| Colorants qs | |
| Preservatives qs | |
| Perfumes qs | |
| Water qs | 100 g |

The shaping lotion obtained is applied readily, and provides the hair style with satisfactory shape-retention.

EXAMPLE 15

Hair styling lotion in a pump bottle

This lotion is prepared by mixing the following ingredients:

| Pseudolatex of Example XIII | 3 g (AS) |
|---|---|
| Colorants qs | |
| Preservatives qs | |
| Perfumes qs | |
| Water qs | 100 g |

When applied to the hair, the lotion obtained gives the hair style good hold.

What is claimed is:

1. A stable pseudolatex comprising in suspension in an aqueous phase particles of non-crosslinked neutralized polyester polyurethane, wherein the polyester polyurethane contains units corresponding to the following formulae (I) and (II):

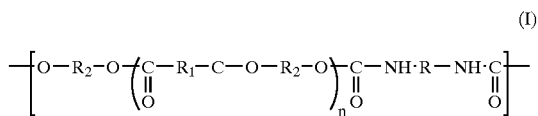

in which:

R represents an alkylene or cycloalkylene radical or a bivalent aromatic radical having from 6 to 15 carbon atoms, n represents an integer such that the molecular weight of the recurring unit is between 400 and 5,000, $R_1$ represents a bivalent radical selected from the group consisting of:
(i) —$(CH_2)_m$—, m being an integer between 2 and 12, and
(ii)

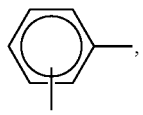

the movable bond being in the ortho, meta or para position, $R_2$ represents a bivalent radical selected from the group consisting of:

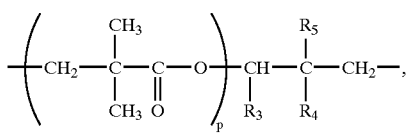

(a)

$R_3$ representing a hydrogen atom or a branched alkyl radical having from 1 to 3 carbon atoms, $R_4$ representing a hydrogen atom or a linear or branched alkyl radical having from 1 to 4 carbon atoms, $R_5$ representing a linear or branched alkyl radical having from 1 to 4 carbon atoms, and p being 0 or 1;

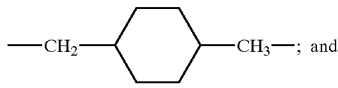

(b)

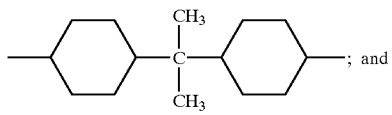

(c)

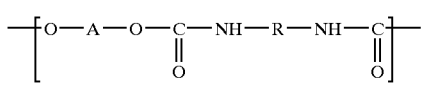

(II)

in which

R is us defined above for the units of formula (I),

A represents an alkylene radical having from 2 to 20 carbon atoms, substituted with a sulphonic acid function, or interrupted by a tertiary nitrogen atom;

wherein the mole ratio between the units (II) and units (I) being between 1:1 and 10:1, wherein the sulphonic acid function is neutralized with a neutralizing agent selected from the group consisting of an inorganic base and an organic base, and the tertiary nitrogen atom is neutralized with a neutralizing agent selected from the group consisting of an inorganic acid and an organic acid, the degree of neutralization being between 20 and 100%, and wherein the average diameter or the particles is between 5 and 300 nm.

2. A stable pseudolatex comprising in suspension in an aqueous phase particles of non-crosslinked neutralized polyester polyurethane, wherein the polyester polyurethane consists of units consisting of formulae (I) and (II), and optionally of units of formula (III):

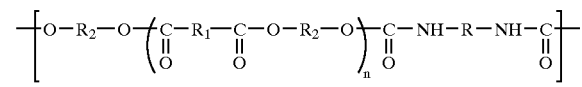

(I)

in which:

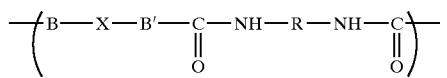

(III)

in which:

R is as defined in claim 1 for the units of formula (I),

B and B', which are identical or different, represent —O— or —NH—, it not being possible for B and B' simultaneously to represent —O—, and X represents an alkylene or cycloalkylene radical having from 2 to 12 carbon atoms or a bivalent aromatic radical having from 6 to 12 carbon atoms.

3. Stable pseudolatex according to claim 2, wherein the molecular weight of said polyester polyurethane, measured by steric exclusion chromatography, is comprised between 4,000 and 500,000.

4. Stable pseudolatex according to claim 2, wherein the molecular weight of said polyester polyurethane, measured by steric exclusion chromatography, is comprised between 6,000 and 200,000.

5. Stable pseudolatex according to claim 2, wherein the average size of the particles is between 10 and 250 nm.

6. Stable pseudolatex according to claim 2, wherein the size polydispersity of the particles, measured by quasi-elastic light scattering, is less than 0.5.

7. Stable pseudolatex according to claim 2, wherein the size polydispersity of the particles, measured by quasi-elastic light scattering, is between 0.05 and 0.4.

8. Stable pseudolatex according to claim 2, wherein in said polyester polyurethane, the mole ratio between the units (II) and the unite (I) is between 1:1 and 5:1.

9. Stable pseudolatex according to claim 2, wherein in said polyester polyurethane, the radical R is selected from the group consisting of hexamethylene, 4,4'-biphenylenemethane, 2,4-tolylene, 2,6-tofylene, 1,5-naphtylene, p-phenylene and 4,4'-methylene-bis (cyclohexyl) radicals and a bivalent radical derived from isophorone.

10. Stable pseudolatex according to claim 2, wherein in said polyester polyurethane, the radical R is selected from the group consisting of 4,4'-biphenylenemethane and 4,4-methylone-bis (cyclohexyl) radicals.

11. Stable pseudolatex according to claim 2, wherein in said polyester polyurethane $R_2$ represents a bivalent radical formula:

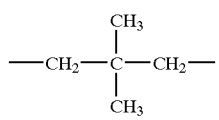

and $R_1$ represents —$(CH_2)_8$— or a p-phenylene radical.

12. Stable pseudolatex according to claim 2, wherein in said polyester polyurethane the bivalent radical A of thy unit of formula (II) is chosen from the group consisting of:

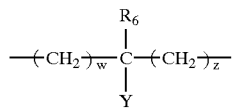

$R_6$ representing a linear or branched alkyl radical having from 1 to 3 carbon atoms, Y representing a carboxylic acid group, or a salt thereof and w and z, which are identical or different, representing an integer between 1 and 5.

13. Stable pseudolatex according to claim 2, wherein in said polyester polyurethane, the radical A of the unit of formula (II) is

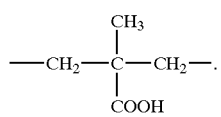

14. Stable pseudolatex according to claim 2, wherein in said polyester polyurethane:

the radical R is selected from the group consisting of 4,4'-biphenylenemethane and 4,4'-methylene-bis (cyclohexyl) radicals, $R_2$ represents a bivalent radical of formula:

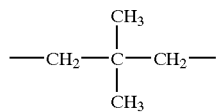

$R_1$ represents —$(CH_2)_8$— and/or a p-phenylene radical.

15. Stable pseudolatex according to claim 14, wherein in said polyester polyurethane, the radical A of the unit of formula (II) is

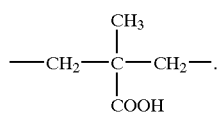

16. Stable pseudolatex according to claim 15, wherein said polyester polyurethane does not contain units of formula (III).

17. Cosmetic composition comprising the pseudolatex according to claim 16 in a cosmetic carrier.

18. Cosmetic composition according to claim 17, wherein the pseudolatex is present in a proportion of between 0.5 and 30% by weight relative to the total weight of the cosmetic composition.

19. Cosmetic composition according to claim 17, wherein the pseudolatex is present in a proportion of between 1 and 25% by weight relative to the total weight of the cosmetic composition.

20. Stable pseudolatex according to claim 2, wherein said polyester polyurethane does not contain units of formula (III).

21. Stable pseudolatex according to claim 2, wherein in said polyester polyurethane, the mob ratio of the sum of the units of formulae (II) and (III) to the units of formula (I) is an integer between 1 and 10.

22. Stable pseudolatex according to claim 2, wherein in said polyester polyurethane, the mole ratio of the sum of the units of formulae (II) and (III) to the units of formula (I) in an integer between 1 and 5.

23. Stable pseudolatex according to claim 2, wherein in said polyester polyurethane, the bivalent radical —B—X—B'— of the units of formula (III) is selected from the group consisting —NH—$CH_2$—$CH_2$—$CH_2$—NH—, —O—$CH_2$—$CH_2$—NH— and —NH—$CH_2$—$CH_2$—O—.

24. Stable pseudolatex according to claim 2, wherein said polyester polyurethane is made of units of formula (I), (II) and (III), and wherein:

the radical R is selected from the group consisting of 4,4'-biphenylenemethane and 4-4'-methylene bis (cyclohexyl) radicals, $R_2$ represents a bivalent radical of formula:

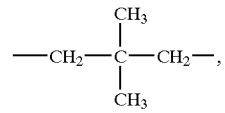

$R_1$ represents —$(CH_2)_8$— and/or a p-phenylene, the radical A is

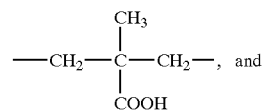

the bivalent radical —B—X—B'— of the units of formula (III) is selected from the group consisting of —NH—$CH_2$—$CH_2$—$CH_2$—NH—, —O—$CH_2$—$CH_2$—NH— and —NH—$CH_2$—$CH_2$—O—.

25. Cosmetic composition comprising the pseudolatex according to claim 24 in a cosmetic carrier.

26. Cosmetic composition according to claim 25, wherein the pseudolatex is a present in a proportion of between 0.5 and 30% by weight relative to the total weight of the cosmetic composition.

27. Cosmetic composition according to claim 25, wherein the pseudolatex is present in a proportion of between 1 and 25% by weight relative to the total weight of the cosmetic composition.

28. Stable pseudolatex according to claim 2, wherein the inorganic base or organic base is selected from the group consisting of sodium hydroxide, potassium hydroxide, ammonia solution, 2-amino-2-methyl-1-propanol (AMP), triethanolamine, triisopropanolamine (TIPA), monoethanolamine, diethanolamine, tris(2-hydroxy-1-propyl)amine, 2-amino-2-methyl-1,3-propanediol (AMPD) and 2-amino-2-hydroxymethyl-1,3-propanediol, and lysine.

29. Cosmetic composition comprising the pseudolatex according to claim 2, in a cosmetic carrier.

30. Cosmetic composition according to claim 29, wherein the pseudolatex is present in a proportion of between 0.5 and 30% by weight relative to the total weight of the cosmetic composition.

31. Cosmetic composition according to claim 29, wherein the pseudolatex is present in a proportion of between 1 and 25% by weight relative to the total weight of the cosmetic position.

32. Stable pseudolatex according to claim 1, wherein the molecular weight of said polyester polyurethane, measured by steric exclusion chromatography, is comprised between 4,000 and 500,000.

33. Stable pseudolatex according to claim 1, wherein the molecular weight of said polyester polyurethane, measured by steric exclusion chromatography, is comprised between 6,000 and 200,000.

34. Stable pseudolatex according to claim 1, wherein the average size of the particles is between 10 and 250 nm.

35. Stable pseudolatex according to claim 1, wherein the size polydispersity of the particles, measured by quasi-elastic light scattering, is less than 0.5.

36. Stable pseudolatex according to claim 1, wherein the size polydispersity of the particles, measured by quasi-elastic light scattering, is between 0.05 and 0.4.

37. Stable pseudolatex according to claim 1, wherein in said polyester polyurethane, the mole ratio between the units (II) and the units (1) is between 1:1 and 5:1.

38. Stable pseudo latex according to claim 1, wherein in said polyester polyurethane, the radical R is selected from the group consisting of hexamethylene, 4,4'-biphenylenemethane, 2,4-tolylene, 2,6-tolylene, 1,5-naphtylene, p-phenylene and 4,4'-methylene-bis (cyclohexyl) radicals and a bivalent radical derived from isophorone.

39. Stable pseudolatex according to claim 1, wherein in said polyester polyurethane, the radical R is selected from the group consisting of 4,4'-biphenylenemethane and 4,4-methylene-bis (cyclohexyl) radicals.

40. Stable pseudolatex according to claim 1, wherein in said polyester polyurethane, R$_2$ represents a bivalent radical formula:

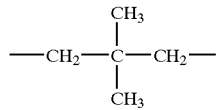

and R$_1$ represents —(CH$_2$)$_8$— or a p-phenylene radical.

41. Stable pseudo latex according to claim 1, wherein in said polyester polyurethane the bivalent radical A of the unit of formula (II) is chosen from the group consisting of:

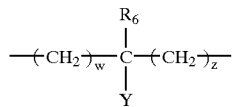 (1)

R$_6$ representing a linear or branched alkyl radical having from 1 to 3 carbon atoms, Y representing a sulphonic acid group or a salt thereof, and w and z, which are identical or different, representing an integer between 1 and 5

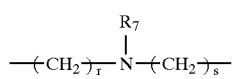 (2)

R$_7$ representing a linear or branched alkyl radical having from 1 to 4 carbon atoms, and r and s, which are identical or different representing an inter between 1 and 10.

42. Stable pseudolatex according to claim 1, wherein in said polyester polyurethane, the bivalent radical A of the unit of formula (II) is

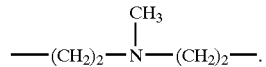

43. Stable pseudolatex according to claim 1, wherein in said polyester polyurethane:
the radical R is selected from the group consisting of 4,4'-biphenylenemethane and 4,4'-methylene-bis (cyclohexyl) radicals,
R$_2$ represents a bivalent radical of formula

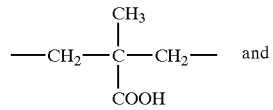 and

R$_1$ represents —(CH$_2$)$_8$— and/or a p-phenylene.

44. Stable pseudolatex according to claim 43, wherein in said polyester polyurethane, the radical A of the unit of formula (II) is

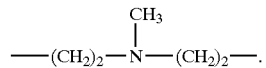

45. Cosmetic composition comprising the pseudolatex according to claim 44 in a cosmetic carrier.

46. Cosmetic composition according to claim 45, wherein the pseudolatex is present in a proportion of between 0.5 and 30% by weight relative to the total weight of the cosmetic composition.

47. Cosmetic composition according to claim 45, wherein the pseudolatex is present in a proportion of between 1 and 25% by weight relative to the total weight of the cosmetic composition.

48. Stable pseudolatex according to claim 1, wherein said polyester polyurethane further contains units corresponding to the following formula (III):

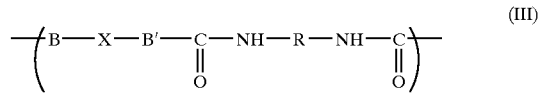 (III)

in which:
R is as defined in claim 1, for the units of formula (I),
B and B', which are identical or different, represent —O— or —NH—, it not being possible far B and B' simultaneously to represent —O—, and
X represents an alkylene or cycloalkylene radical having from 2 to 12 carbon atoms or a bivalent aromatic radical having from 6 to 12 carbon atoms.

49. Stable pseudolatex according to claim 48, wherein in said polyester polyurethane, the mole ratio of the sum of the units of formulae (II) and (III) to the units of formula (I) is an integer between 1 and 10.

50. Stable pseudolatex according to claim 48, wherein in said polyester polyurethane, the mole ratio of the sum of the units of formulae (II) and (III) to the units of formula (I) is an integer between 1 and 5.

51. Stable pseudolatex according to claim 48, wherein in said polyester polyurethane, the bivalent radical —B—X—

B'— of the units of formula (III) is selected from the group consisting of —NH—CH$_2$—CH$_2$—NH—, —O—CH$_2$—CH$_2$—NH— and —NH —CH$_2$—CH$_2$—O—.

52. Stable pseudolatex according to claim 51, wherein in said polyester polyurethane, the radical R is selected from the group consisting of 4, 4'-biphenylenemethane and 4,4'-methylene bis (cyclohexyl) radicals, R$_2$ represents a bivalent radical of formula:

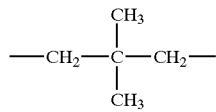

R$_1$ represents —(CH$_2$)$_8$— and/or p-phenylene, and
A represents

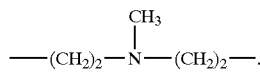

53. Cosmetic composition comprising the pseudolatex according to claim 48 in a cosmetic carrier.

54. Cosmetic composition according to claim 53, wherein the pseudolatex is a present in a proportion of between 0.5 and 30% by weight relative to the total weight of the cosmetic composition.

55. Cosmetic composition according to claim 53, wherein the pseudolatex is present in a proportion of between 1 and 25% by weight relative to the total weight of the cosmetic composition.

56. Stable pseudolatex according to claim 1, wherein the inorganic base or organic base is selected from the group consisting of sodium hydroxide, potassium hydroxide, ammonia solution, 2-amino-2-methyl-1-propanol (AMP), triethanolamine, triisopropanolamine (TIPA), monoethlanolamine, diethanolamine, tris(2-hydroxy-1-propyl)amine, 2-amino 2-methyl-1,3-propanediol (AMPD), 2-amino-2-hydroxymethyl-1,3-propanediol and lysine.

57. Stable pseudolatex according to claim 1, wherein the inorganic acid or organic acid is selected from the group consisting of hydrochloric acid, lactic acid, glycolic acid and mandelic acid.

58. Cosmetic composition comprising the pseudolatex according to claim 1 in a cosmetic carrier.

59. Cosmetic composition according to claim 58, wherein the pseudolatex is present in a proportion of between 0.5 and 30% by weight relative to the total weight of the cosmetic composition.

60. Cosmetic composition according to claim 58, wherein the pseudolatex is present in a proportion of between 1 and 25% by weight relative to the total weight of the cosmetic composition.

* * * * *